(12) United States Patent
Eineren et al.

(10) Patent No.: US 9,922,242 B2
(45) Date of Patent: Mar. 20, 2018

(54) SYSTEMS AND METHODS FOR PREDICTING THE OUTCOME OF A STATE OF A SUBJECT

(71) Applicant: AGRICAM AB, Linköping (SE)

(72) Inventors: Ellinor Eineren, Linköping (SE);
Landy Toth, Doylestown, PA (US);
Jorgen Ahlberg, Linköping (SE)

(73) Assignee: AGRICAM AB, Linkoping (SE)

( * ) Notice: Subject to any disclaimer, the term of this patent is extended or adjusted under 35 U.S.C. 154(b) by 90 days.

(21) Appl. No.: 14/648,789

(22) PCT Filed: Nov. 26, 2013

(86) PCT No.: PCT/IB2013/003123
§ 371 (c)(1),
(2) Date: Jun. 1, 2015

(87) PCT Pub. No.: WO2014/083433
PCT Pub. Date: Jun. 5, 2014

(65) Prior Publication Data
US 2015/0302241 A1    Oct. 22, 2015

Related U.S. Application Data

(60) Provisional application No. 61/781,307, filed on Mar. 14, 2013, provisional application No. 61/732,380, filed on Dec. 2, 2012.

(51) Int. Cl.
*G06K 9/00* (2006.01)
*A01J 5/007* (2006.01)
(Continued)

(52) U.S. Cl.
CPC .......... *G06K 9/00362* (2013.01); *A01J 5/007* (2013.01); *A01J 5/0175* (2013.01); *A01K 29/005* (2013.01);
(Continued)

(58) Field of Classification Search
CPC .... G06K 9/00362; G06N 99/005; G06N 5/04; A01J 5/007; A01J 5/0175; A01K 29/005;
(Continued)

(56) References Cited

U.S. PATENT DOCUMENTS 5,474,085 A     12/1995  Hurnik et al.
2004/0019269 A1   1/2004  Schaefer et al.
(Continued)

FOREIGN PATENT DOCUMENTS

CN    101404874 A    4/2009
CN    101431890 A    5/2009
(Continued)

OTHER PUBLICATIONS

Office Action for corresponding Chinese Application No. 201380062925.2 dated Jul. 6, 2016.
(Continued)

*Primary Examiner* — Amandeep Saini
(74) *Attorney, Agent, or Firm* — Carter, DeLuca, Farrell & Schmidt, LLP

(57) ABSTRACT

Systems and methods for improving the health and wellbeing of subjects in an industrial setting are disclosed. The systems may include a camera arranged so as to observe one or more features of a subject, and a processor, coupled to the camera, the processor configured to analyze one or more images obtained therefrom, to extract one or more features from the image(s) of the subject, and to analyze one or more of the features, or sub features nested therein to predict an outcome of a state of the subject. In particular the system may be configured to generate a diagnostic signal (e.g. an outcome, fever, mastitis, virus, bacterial infection, rut, etc.) based upon the analysis.

31 Claims, 4 Drawing Sheets

(51) Int. Cl.
  *A01J 5/017*  (2006.01)
  *A01K 29/00* (2006.01)
  *G06N 5/04*  (2006.01)
  *G06N 99/00* (2010.01)
  *A61B 5/00*  (2006.01)

(52) U.S. Cl.
  CPC ............. *G06N 5/04* (2013.01); *G06N 99/005* (2013.01); *A61B 5/7275* (2013.01); *A61B 2503/40* (2013.01); *F04C 2270/0421* (2013.01)

(58) Field of Classification Search
  CPC ........... F04C 2270/0421; A61B 5/7275; A61B 2503/40
  USPC ....................................................... 382/110
  See application file for complete search history.

(56) References Cited

U.S. PATENT DOCUMENTS

| | | | | |
|---|---|---|---|---|
| 2004/0141635 | A1* | 7/2004 | Liang | A61B 5/1113 382/110 |
| 2011/0054338 | A1 | 3/2011 | Linker et al. | |
| 2011/0117025 | A1* | 5/2011 | Dacosta | A61B 5/0059 424/9.6 |
| 2012/0059779 | A1 | 3/2012 | Syed et al. | |

FOREIGN PATENT DOCUMENTS

| | | |
|---|---|---|
| NZ | 586888 A | 10/2011 |
| WO | 0057164 A1 | 9/2000 |
| WO | 2009/022003 A1 | 2/2009 |
| WO | 2010/127023 A1 | 11/2010 |
| WO | 2012/080275 A1 | 6/2012 |
| WO | 2012/129657 A1 | 10/2012 |
| WO | 2013/058985 A1 | 4/2013 |
| WO | 2013/149038 A1 | 10/2013 |
| WO | 2013/172963 A1 | 11/2013 |

OTHER PUBLICATIONS

International Search Report issued in corresponding application No. PCT/IB2013/003123 dated Jun. 3, 2014.
Second Chinese Office Action for Chinese Appln. No. CN 2013800629252 dated Mar. 2, 2017.
Australian Examination Report No. 2 for Australian Appln. No. AU 2013350867 dated Mar. 10, 2017.
Examination Report for corresponding Australian Application No. 2013350867 dated Jun. 26, 2017.
Office Action for corresponding Chinese Application No. 2013800629252 dated Aug. 28, 2017.
New Zealand First Examination Report for NZ 708197 dated Aug. 7, 2017.

* cited by examiner

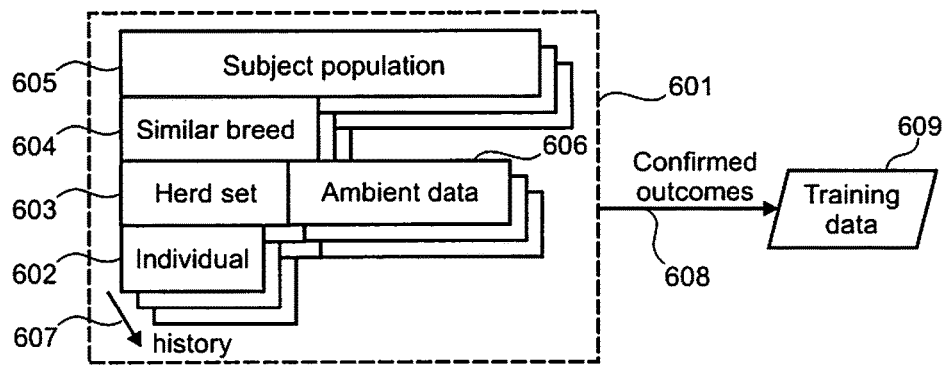
Fig 7
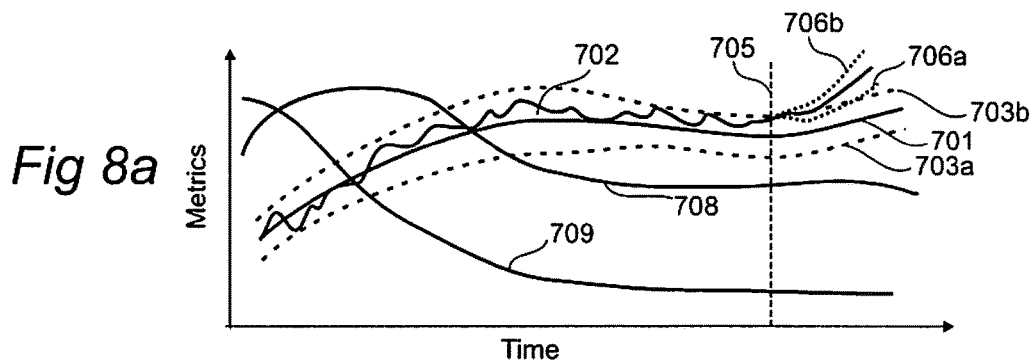
Fig 8a
Fig 8b
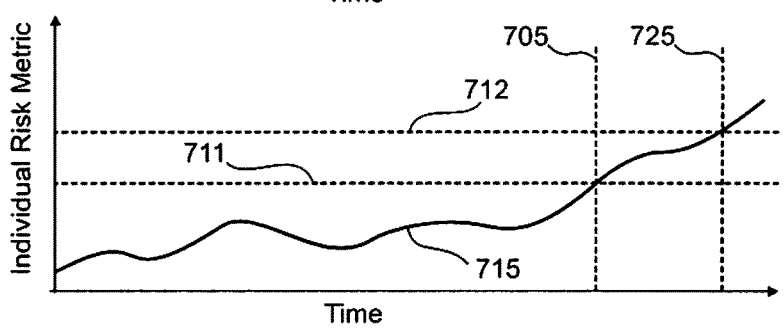
Fig 9
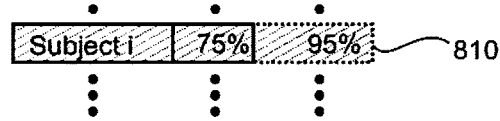

SYSTEMS AND METHODS FOR PREDICTING THE OUTCOME OF A STATE OF A SUBJECT

BACKGROUND

Technical Field

The present disclosure is directed to systems and methods for analyzing subjects in a work environment. Furthermore, the disclosure relates to systems and methods for analyzing health and wellness of living beings such as livestock without substantially impacting workflow, movement patterns in the vicinity thereof, or the like.

Background

In industrialized farming, the health and wellbeing of livestock (e.g. cows, fish, poultry, swine, sheep, etc.) is critical to maintaining the ongoing operation and sustainability of an organization (such as a farm, a distribution chain, etc.). Of particular relevance, improved management of cattle is of interest to industrial institutions, food distribution networks, and farmers. Events such as breakouts of disease (e.g. infection, mastitis, influenza, etc.) can wipe out entire herds and/or otherwise adversely affect production of milk or produce. For example, clinical and subclinical mastitis may have significant negative impact on milk productivity and quality with diagnosis of clinical mastitis often prompting isolation of animals from a herd and even emergency slaughter. Although clinical mastitis is treated today with antibiotics, subclinical mastitis is not treated at all.

In addition, the optimization of breeding programs and the like may have significant impacts on the bottom line for such organizations.

In general, although monitoring of livestock may be very useful for assisting with herd management, the practicality of the monitoring process may be hampered by the need for maintaining an un-obscured and/or un-fouled view of the subjects over prolonged periods of time, coupled to the need to work amid soiled and/or cluttered environments, and in an unobtrusive manner (i.e. without substantially altering the environment, movement paths, workflow, etc.).

SUMMARY

One objective of the present disclosure is to provide a system and a method for improving the health and wellbeing of animals in an industrial setting.

Another objective is to provide a system and a method for improving the management of operations (e.g. milking, breeding, cleanliness, etc.) of livestock.

Another objective is to provide a system and method for predicting the health outcome of a subject within an environment (i.e. during a process, while moving through the environment, during milking, queuing, etc.).

Yet another objective is to provide a system and method for predicting the onset of sickness in a subject or population of subjects.

The above objectives are wholly or partially met by systems, and methods described herein. In particular, features and aspects of the present disclosure are set forth in the appended claims, following description, and the annexed drawings.

According to a first aspect there is provided a system for predicting the health outcome of a subject in an environment including a camera situated within the environment configured to generate one or more images and/or a video sequence including at least a portion of a feature of the subject; and a processor, configured to identify and segment at least a portion of the feature from one or more of the images and/or video sequence to form one or more segmented features, to calculate one or more metrics from the segmented features, and to predict the health outcome of the subject based upon one or more of the metrics.

In aspects, the system may include a database configured in communication with the processor. The database may be configured to store one or more of the images and/or video sequences, one or more reference features, one or more of the segmented features, and/or one or more of the metrics. The processor may be arranged so as to communicate with the database.

In aspects, the processor may be configured to compare one or more of the reference features with one or more of the segmented features to predict the health outcome of the subject, the processor may be arranged to receive one or more environmental parameters to predict the health outcome of the subject, and/or the processor may be configured to calculate one or more environmental parameters from one or more of the images and/or video sequences to predict the health outcome of the subject.

In aspects, the processor may be configured to segment at least a portion of the feature from each of a plurality of images and/or a video sequence to form a collection of segmented feature portions, and to combine the segmented feature portions to form a representative segmented feature for use in predicting the health outcome of the subject.

In aspects, the processor may be configured to segment at least a portion of the feature in the presence of an obstruction (e.g. a body part, a leg, a tail, a dirty lens, an object, a milking machine component, a combination thereof, or the like).

In aspects, the camera (a digital camera, a visible light camera, a near-infrared reflectance imaging camera, an infrared camera, a fluorescence imaging camera, a UV imaging camera, a thermal imaging camera, a 3D camera, a combination thereof, or the like) may be configured to generate the images and/or video sequence while the subject is moving within the environment. In aspects, the system may include a plurality of cameras, each camera arranged so as to image a different portion of the feature and/or an alternative feature on the subject.

In aspects, the processor may be configured to send out an alert based upon the health outcome prediction.

According to another aspect there is provided use of a system in accordance with the present disclosure in a livestock management system.

According to yet another aspect there is provided, use of a system in accordance with the present disclosure to predict the onset of mastitis in a lactating animal.

According to another aspect there is provided, use of a system in accordance with the present disclosure to predict the onset of rut in an animal.

According to yet another aspect there is provided, use of a system in accordance with the present disclosure to provide an input for an automated milking system.

According to another aspect there is provided, a method for predicting the health outcome of a subject in an environment including, imaging the subject to produce one or more images thereof; identifying one or more features in one or more of the images; segmenting out at least a portion of the identified features from one or more of the images to form one or more segmented features; calculating one or more metrics from the segmented features; and predicting the health outcome of the subject based upon one or more of the metrics.

In aspects, the imaging may be performed over a period of time while the subject is moving through the environment.

In aspects, the method may include segmenting out a plurality of segmented features from a plurality of images and generating a representative segmented feature for use in the calculation of the metrics.

In aspects, the imaging may be performed before, during, and/or after a procedure (e.g. a milking procedure, administration of a medication, a mating process, a sporting event, a training procedure, etc.).

In aspects, the method may include comparing the segmented features to a reference feature from the subject, to an environmental parameter, comparing the segmented features and/or metrics to a previously obtained segmented feature and/or metric, and/or comparing the segmented features and/or metrics from the subject to those obtained from a family of related subjects as part of the prediction.

In aspects, the method may include alerting a user and/or a system (e.g. a monitoring system, a livestock management system, an automatic milking system, an automated treatment system, etc.) to the prediction.

In aspects, the health outcome may be an infection, rut, a disease state, etc.

In aspects, the method may include identifying on one or more of the images of the subject the location of the potential infection.

In aspects, the imaging may be performed with a system in accordance with the present disclosure, a camera (e.g. a digital camera, a visible light camera, a near-infrared reflectance imaging camera, an infrared camera, a fluorescence imaging camera, a UV imaging camera, a thermal imaging camera, a 3D camera, a combination thereof, or the like), etc.

In aspects, the prediction may be at least partially performed by a predictive model.

According to yet another aspect there is provided, a method for predicting the health outcome of a partially obstructed subject moving through an environment including: imaging the subject to produce a plurality of partially obstructed images thereof; identifying one or more features in one or more of the partially obstructed images; segmenting out at least a portion of the identified features from a plurality of the images to form a group of partially segmented features; merging the partially segmented features to form a representative segmented feature; calculating one or more metrics from the representative segmented feature; and predicting the health outcome of the subject based upon one or more of the metrics.

In aspects, the method may include storing the metrics and/or representative segmented features for future recall, and/or comparing one or more stored metrics and/or representative segmented features to one or more of the representative segmented features and/or metrics as part of the prediction.

According to yet another aspect there is provided, a system for monitoring a subject in an environment including a camera arranged so as to observe one or more features of the subject, and a processor, coupled to the camera, the processor configured to analyze one or more images obtained therefrom, to extract one or more features from the image(s) of the subject, and to analyze one or more of the features, or sub features nested within a feature to predict an outcome of a state of the subject.

In aspects, the subject may be a living being (e.g. a human, an animal, a fish, a plant, etc.), an animal (e.g. livestock, a cow, a sheep, a pig, a horse, a deer, etc.), a plant, a manufacturing process, a wilderness environment, a gas, a combination thereof, or the like.

In aspects, the feature may be an udder, a part of an udder, a teat, a muzzle, a nostril, a hair pattern, a patch of skin, a hoof, a mouth, an eye, genitalia, a combination thereof, or the like.

In aspects, one or more of the metrics may include thermographic data, color, shape, size data, a thermal metric, an average temperature, a thermal gradient, a temperature difference, a temperature range, a thermal map, a physiological parameter, changes therein, or combination thereof relating to one or more of the segmented features.

In aspects, a monitoring system and/or a method in accordance with the present disclosure may be configured to generate a diagnostic signal (e.g. an outcome, fever, mastitis, virus, bacterial infection, rut, etc.) based upon the analysis of one or more of the images.

According to yet another aspect there is provided, a method for imaging a subject, including obtaining one or more images of the subject with a camera through a window pane, assessing the cleanliness of the window pane from one or more of the images to create a cleanliness factor; and cleaning the window pane based on the cleanliness factor. In aspects, the method may include releasing one or more of the images for analysis based upon the cleanliness factor; exposing the window pane to the subject; and/or locating the subject.

According to yet another aspect there is provided, a monitoring system for assessing a subject including a controller configured to generate one or more control signals; a camera module in accordance with the present disclosure configured to obtain images from at least an aspect of the subject and to convey the images to the controller, the camera module configured to respond to one or more of the control signals; and a sensing subsystem and/or a surveillance camera configured to convey the location, orientation, and/or identification of the subject to the controller, the controller configured to analyze the location, orientation, and/or identification of the subject to produce one or more of the control signals.

BRIEF DESCRIPTION OF THE DRAWINGS

FIG. 7 shows a method for generating training data in accordance with the present disclosure.

FIGS. 8a-b show a time history graph of metrics for evaluating the outcome of a subject in accordance with the present disclosure.

FIG. 9 shows a user interface for displaying data about a group of subjects in accordance with the present disclosure.

DETAILED DESCRIPTION

Figure 1:
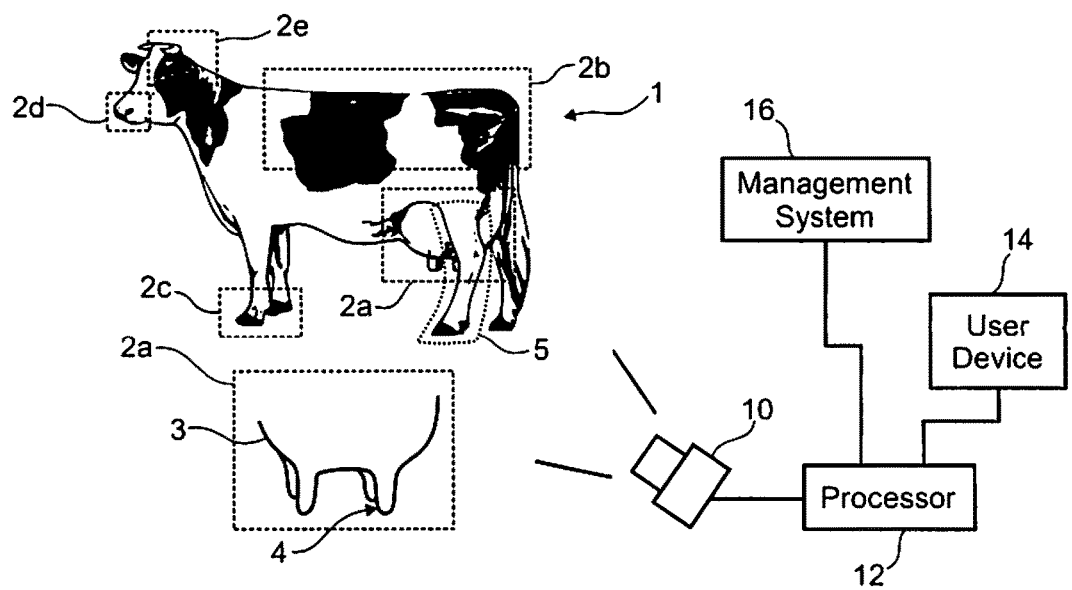
FIG. 1 shows aspects of a system for monitoring a subject in accordance with the present disclosure.

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

By camera is meant, without limitation, a digital camera, a visible light camera, a near-infrared reflectance imaging camera, an infrared camera, a fluorescence imaging camera, a UV imaging camera, a thermal imaging camera, a 3D camera, combinations thereof, and the like.

In aspects, a system in accordance with the present disclosure including a camera may be configured to monitor one or more subjects in an environment into which it is placed (i.e. as part of a surveillance system, an analysis system, an industrial control process, a livestock management system, etc.). A subject may include a machine, a vehicle, a living organism, a human, an animal, livestock, a cow, a plant, combinations thereof or the like. In aspects, the system may be configured to monitor an aspect of the environment (e.g. a gas, chemical specie, an exhaust leak, an ambient temperature, a processing line, feeding equipment, etc.). In aspects, the environment may include a manufacturing plant, a green house, a concert hall, a theatre, a crowded landscape, a shopping center, forest trail, a barn, a field, a crop, a ski resort, or the like. In aspects, the system may be coupled to a process (e.g. a milking process, a fabrication procedure, a breeding process, a feeding process, etc.).

In aspects, a system in accordance with the present disclosure may be configured to analyze one or more aspects of plant-life, a plant, a crop, etc. Such a system may be configured to perform thermography (e.g. passive thermography, active thermography, etc.), near-infrared reflectance imaging, reflectance imaging, fluorescence imaging, combinations thereof, or the like on the plant-life. Such imaging processes may be used to diagnose disease, determine growth efficiency, monitor farming processes, investigate infestations, viral infections, fungal infestations, etc. Such imaging may be performed in generally uncontrolled and/or dirty environments.

In aspects, a system and/or associated camera in accordance with the present disclosure may be configured to monitor one or more subjects within a livestock management environment/process (e.g for management of milking operations, reproductive monitoring, biogas production, grazing, cleaning, biogas containment, etc.). In aspects, the system may be configured to monitor methane gas levels within a barn, monitor methane cloud migration within a barn, detect leakage of methane gas from a barn into a surrounding environment, and the like.

In aspects, a system in accordance with the present disclosure may be used to monitor distribution, leakage, and or properties of a biogas distribution system, a gas management system, gas containment process, and/or biogas harvesting system.

In aspects, a system in accordance with the present disclosure may include a camera and one or more electrical circuits configured to control one or more aspects of the camera (sensors, alignment lighting, reference lights, cooling system, ambient lighting sensors, ambient condition sensors, etc.), image processing circuitry, a cleaning system (e.g. fluid delivery valves, fluid uptake valves, fluid filtering processes, etc.), and/or one or more aspects of a servo-actuation system (e.g. for use in an articulated configuration).

FIG. 1 shows aspects of a system for monitoring a subject in accordance with the present disclosure applied to a livestock monitoring application. A camera module 10 (i.e. a camera optionally including a house, electronics, cleaning aspects, etc. in accordance with the present disclosure) may be included in part of the system in accordance with the present disclosure. The camera module 10 may be positioned near to the flow of traffic of subjects 1, which may be used to register a spatially precise image from a subject 1 (e.g. an animal, a cow, etc.), or a feature (e.g. an udder 2a, part of an udder 3, a teat 4, a pattern 2b, a hoof 2c, a mouth 2d, an eye 2e, genitalia, etc.). The camera module 10 may be coupled to one or more processors 12, at least one processor configured to analyze one or more images captured by the camera module 10. The processor 12 may be coupled to a management system 16 (e.g. a livestock management system, a scheduling system, a veterinarian alert system, an electronic health record system, a network, a cloud data system, etc.) and/or a user device 14 (e.g. a console, a terminal, a software interface, a cell phone, a smartphone, a tablet computer, etc.). The processor may be configured to relay status information, health information, a metric, etc. to the management system 16 and/or the user device 14 in order to provide decision able data relating to the management of the subject 1.

The subject 1 may include one or more obstructions 5 (e.g. a leg, a tail, an arm, clothing, a hat, glasses, a mask, etc.) which may at least partially obstruct one or more of the features 2a-e, 3, 4 from the view of the camera module 10. At times, during a process of monitoring the subject 1, one or more of the obstructions 5 may interfere with a clear view of the desired feature 2a-e, 3, 4. In such situations, an associated image analysis process may be configured to extract at least a portion of the feature 2a-e, 3, 4 in the presence of the obstruction 5 so as to continue with the extraction of one or more health metrics from the subject 1.

In aspects, the camera module 10 may include a protective housing (not explicitly shown), and a surface (not explicitly shown) within the field of view of the camera module 10. The camera module 10 may include a self-cleaning system and/or functionality in order to routinely clean the surface thereof, during use.

In aspects, a monitoring system including a camera module 10 (or equivalently a camera) in accordance with the present disclosure may include one or more systems for detecting the presence and/or identity of the subject 1. Thus the system may include one or more sensing subsystems (e.g. an RFID locating system, a pyrometer, an ultrasonic sensor, a light curtain, etc.) configured to locate and/or identify the subject 1 within range of the camera module 10.

In aspects, the subject 1 may be an animal (e.g. a cow, a sheep, a lamb, a pig, etc.) equipped with an RFID tag (not explicitly shown). A RFID tag reader may be positioned near to one or more camera modules 10 such that as a subject 1 moves within range of the reader (determined via broadcast and receipt of an RF signal between the reader and the RFID tag), the reader may be configured to communicate the control signal to one or more entities in the monitoring system (e.g. the camera module 10, the management system 16, etc.). Upon receipt of the control signal, the camera module 10 may be configured to awaken and continue with operations (e.g. assessing cleanliness, obtaining one or more reading, capture a video, etc.).

In aspects, the camera module 10 may be configured to receive one or more control signals from the processor 12. In aspects, the processor may be configured to receive one or more control signals from the management system 16, the user device 14, etc. Some non-limiting examples of such control signals include powering up the camera module 10, placing it into standby, requesting data capture from a subject 1, requesting delivery of data from the camera module, and the like.

Figure 2:
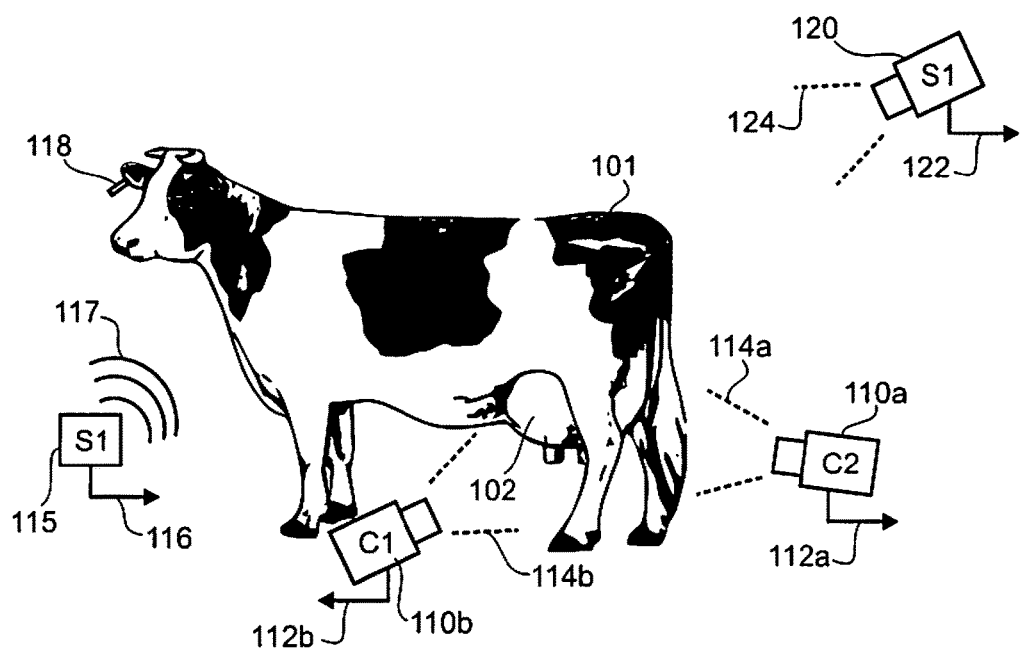
FIG. 2 shows aspects of a system in accordance with the present disclosure.

FIG. 2 shows aspects of a monitoring system in accordance with the present disclosure applied to a livestock management application. The monitoring system may include one or more camera modules 110a-b, each in accordance with the present disclosure. One or more of the camera modules 110a-b may include a camera with a field of view 114a-b, oriented so as to face a subject 101 (e.g. a scene, a work station, a living target, an animal, a cow, etc.) or a region of high traffic for subjects. In aspects, the camera modules 110a-b may be arranged in a monitoring environment, such that during a routine (e.g. milking, feeding, etc.) the subject 101 may pass into the field of view 114a-b thereof. The camera modules 110a-b may be coupled to a processor, a management system, a controller, a power source, etc. via one or more signal transfer lines 112a-b.

In aspects, one or more of the camera modules 110a-b may include a protective cover (not explicitly shown), each protective cover configured so as to be actuate able during use (i.e. so as to provide intermittent cover for one or more windows/lenses on the camera modules 110a-b during use).

In aspects, the monitoring system may include one or more sensing subsystems 115 (e.g. an RFID locating system, a pyrometer, an ultrasonic sensor, a light curtain, etc.) and/or surveillance cameras 120 configured so as to assess the subject 101 and/or an environment in the vicinity of the camera modules 110a-b (i.e. a space encompassing at least a portion of the field of view 114a-b of one or more of the camera modules 110a-b) during use. The surveillance camera 120 may include a field of view 124 and a communication line 122 to communicate an image and/or video feed of the subject 101 and/or an associated environment (i.e. for detecting ambient conditions, assessing cleanliness, collecting reference data, etc.), in which the subject 101 resides, to one or more aspects of the monitoring system. In aspects, the subject 101 may wear or be coupled to an identification tag 118, the tag 118 may be configured to store and/or collect identification information, physiological data, environmental data, kinematic data (e.g. movement, location tracking information, etc.) related to and/or from the target 101. In aspects, one or more of the sensing subsystems 115 may include a communication line 116 to communicate one or more obtained signals to one or more aspects of the monitoring system.

One or more of the camera modules 110a-b may include a communication line 112a-b to communication an image and/or video feed, a status update, receive commands, power, status update requests, etc. to one or more aspects of the monitoring system.

In aspects, one or more of the sensing subsystems 115 may include an RFID reader. The RFID reader may be configured to locate and/or identify one or more tags 115 placed on the subject 101 or in the vicinity thereof. The RFID reader may be configured to periodically broadcast an RF signal 117 to communicate with a local ID tag 118 which may be placed onto the subject 101. The sensing subsystem 115 may be configured to communicate a target acquired signal 116, to one or more aspects of the monitoring system (e.g. may be to one or more of the camera modules 110a-b). In one non-limiting example, the subject 101 may be an animal (e.g. a cow, a sheep, a lamb, a pig, etc.) equipped with an RFID tag 118. A RFID tag reader 115 may be positioned near to one or more camera modules 110a-b such that as the subject 101 moves within range of the reader 115 (determined via broadcast and receipt of an RF signal 118 between the reader 115 and the tag 118), the reader may be configured to communicate a control signal 116 to one or more entities in the monitoring system. Upon receipt of the control signal 116 or a signal derived therefrom, one or more of the camera modules 110a-b may be configured to awaken and continue with operations (e.g. opening a protective cover, assessing cleanliness, obtaining one or more reading of the subject 101, capture a video from the subject 101, etc.).

In aspects, a sensing subsystem 115 and/or tag 118 may be configured to communicate one or more of identification data, physiological data, environmental data (e.g. temperature, humidity, light level, etc.) to one or more aspects of the monitoring system.

The monitoring system may include an array of camera modules each in accordance with the present disclosure. One or more camera modules may be operated synchronously with one or more of the other modules, surveillance cameras, etc. via coordination by the monitoring system, or the like.

In an application relating to industrial monitoring, one or more camera modules may be positioned high above the assembly line, conveyor systems, etc. Such a camera module may be configured so as to observe one or more macro sized regions of the manufacturing space, monitor movement of subjects throughout the environment, collect data from one or more features simultaneously from a plurality of subjects, capture lighting aspects within the environment, capture heat signatures from the environment, combinations thereof, or the like.

Figure 3:
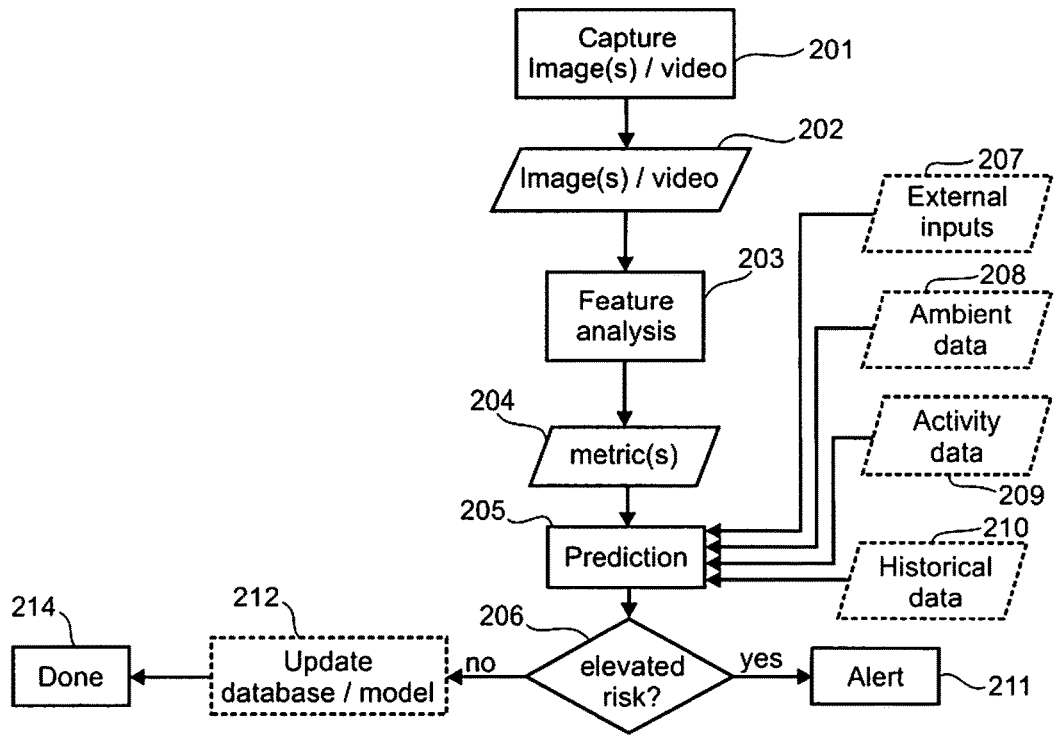
FIG. 3 shows a method for predicting the outcome of a subject in accordance with the present disclosure.

FIG. 3 shows a method for predicting the outcome of a subject in accordance with the present disclosure. By outcome is meant, without limitation, predicting a health outcome (e.g. a fever, an infection, mastitis, a healing event, a growth event, etc.), a fertility cycle (i.e. determining when a subject is ovulating, etc.), combinations thereof, or the like. The method may include capturing image(s) and/or video 201 of the subject in an environment each in accordance with the present disclosure. Capturing images(s) and/or video 201 may be completed by one or more cameras and/or camera modules each in accordance with the present disclosure.

The method may include storing the image(s) and/or video 202 in memory, a local storage medium, on a network storage system, a cloud system, etc. The method may include analyzing a feature 203 from the subject in order to extract one or more metrics (e.g. a thermal metric, an average temperature, a temperature gradient, a temperature difference, a temperature range, a physiological parameter, combinations thereof, or the like) from the image(s) and/or video. In aspects, the step of analyzing a feature may include identifying the subject, identifying the feature(s) of interest on the subject, segmenting the feature, extracting one or more metrics from the segmented feature, combinations thereof, or the like.

In aspects, the step of analyzing a feature may include determining if a feature is at least partially obstructed, and, if so, segmenting at least part of the feature that is unobstructed, from which metrics may be extracted. In aspects, a partially obstructed feature may be segmented across a number of images (i.e. across several frames of a video). In such aspects, at least a portion of the feature may be segmented in each image (such as picture, a frame of a video sequence, etc.). The collection of segmented feature portions may be analyzed separately to extract a collection of associated metrics. The collection of metrics may then be merged into a representative metric, for use in other steps of the method. In aspects, the collection of segmented feature portions may be grouped together with a merging algorithm so as to generate a more complete segmented feature portion, and associated metric(s) may be extracted therefrom for use in other steps in the method.

The method may include storing the metrics 204 in memory, a local storage medium, on a network, in a database, etc. for use in other steps of the method.

The method may include predicting an outcome 205 of the subject. The step of predicting an outcome 205 may include comparing the metric(s) 204 with one or more of external inputs 207, ambient data 208, activity data 209, historical data 210 (i.e. from a database of metrics), stored history of outcomes (e.g. for the subject, a family, a herd, a group of subjects, etc.), metric history of the subject, metric history of a collection of subjects (e.g. a family, a herd, etc.), or the like. And, based upon the comparison, predicting the state and/or future state of the subject (e.g. fever, mastitis, onset of mastitis, ovulation, time until the onset of ovulation, etc.).

In aspects, the step of prediction 205 may include providing one or more metrics 204, external inputs 207, ambient data 208, activity data 209, historical data 210 (i.e. from a database of metrics, etc.) to a predictive model in accordance with the present disclosure, and assessing the prediction provided from the predictive model.

A prediction may be provided in the form of a risk value, an accumulating risk value (i.e. whereby the risk of a negative outcome increases with periods of sustained, yet low to moderate risk), or the like. Such predictions may be compared with a predetermined diagnostic value, or the like to render a decision about the subject.

The method may include assessing a risk value 206 to determine if action should be taken with regard to the state of health, fertility, etc. of the subject. In the case that action should be taken, the method may include generating an alert 211, such an alert may be conveyed to one or more aspects of the monitoring system, to a veterinarian, to a scheduling system, to a user device, to a livestock management system, to a hospital, etc.

In the case that the subject is considered healthy (i.e. no action necessary at this time), the method may include a step of updating 212 the historical data, updating the predictive model, scheduling software, etc. and then completing 214 the outcome prediction process for the associated subject.

One or more aspects of the method may be performed on a processor in accordance with the present disclosure, in a management system in accordance with the present disclosure, in a connected cloud computing center, with combinations thereof, or the like.

In aspects, some non-limiting examples of external inputs 207 which may be used during prediction 205 include a user defined alert level (i.e. a user defined statement of risk), a local weather report, a risk level for a related population (i.e. a risk level from a nearby center, farm, city, etc.), a control signal (i.e. associated with ventilation of a facility, an infrared heating source, etc.), externally applied sensory data (e.g. milk conductivity data, a lab result, a milk yield, etc.).

In aspects, some non-limiting examples of ambient data 208 which may be used during prediction 205 include a local temperature level, a local HVAC control signal, local cloud conditions, a local humidity, an ambient light level, an ambient infrared light level, combinations thereof, or the like.

In aspects, some non-limiting examples of activity data 209 may include a path history for the subject (e.g. to assess the distance walked by the subject over a recent history, to assess the locations visited by the subject over a recent history, etc.), a recent movement rate of the subject (i.e. so as to correlate with an associated increase in metabolism and skin temperature rise), a heart-rate signal, a breathing rate signal, a breath gas analysis, or the like. Such values maybe provided for an individual subject, a family, a family member, a herd, a class, etc. for use in the prediction.

In aspects, some non-limiting examples of historical data 210 may include a history of metrics, outcomes, recent events (e.g. surgeries, milking events, feeding events, milk yield, food consumption amounts, duration of feeding, medication administration, checkups, etc.) for an individual subject, for the subject, for a family of subjects, for a herd, for a class, or the like.

Such information may be used in conjunction with metric (s) in order to improve the robustness of the predictive outcome of the prediction 205.

Figure 4:
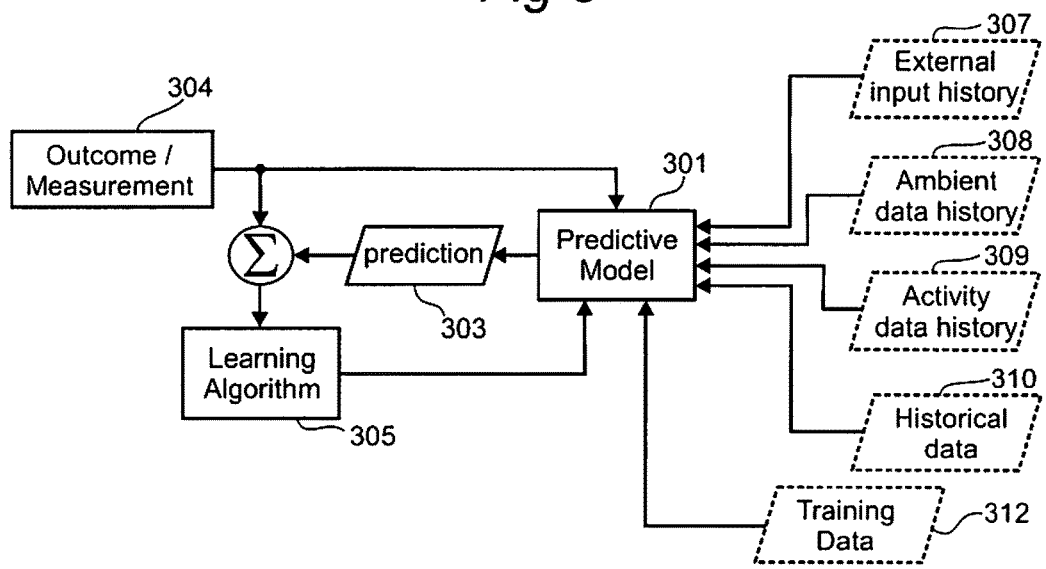
FIG. 4 shows aspects of a model for predicting the outcome of a subject in accordance with the present disclosure.

FIG. 4 shows aspects of a model 301 for predicting the outcome of a subject in accordance with the present disclosure (e.g. as part of a prediction step 205, as part of training process, etc.). The predictive model 301 may include a mathematical model (e.g. a transfer function, a nonlinear system, a neural network, a fuzzy logic network, a Bayesian network, etc.) for generating a potential outcome or risk level for a subject, given inputs in the form of one or more measurements/outcomes 304, one or more external inputs 207 or history of external inputs 307, one or more ambient data points 208 or a history of ambient data points 308, one or more activity data points 209 and/or a history of activity data points 309, one or more historical metric(s) 210, 310, one or more training datasets 312, each in accordance with the present disclosure. In aspects, each such input may be related to the subject, a group of subjects, a family of subjects, a family member, a herd, a population, combinations thereof or the like.

The predictive model 301 may be configured to generate a prediction 303 (e.g. a risk state for a subject, a diagnosis, a relative risk for a group, a future prediction of a metric, etc.) from the collection of inputs. In aspects, the predictive model 301 may include a transfer function, a nonlinear relationship, a statistical model, a feed forward predictive model, a parametric model, combinations thereof, and the like.

In aspects, a learning algorithm 305 may be coupled to the model to compare a prediction 303 with a measured outcome 304, and so influence and/or adapt the model 301 so as to improve the predictive value thereof. Some non-limiting examples of such learning algorithms 305 include Kalman filters, least squares filters, extended Kalman filters, fast Kalman filters, node decoupled Kalman filters, temporal difference learning algorithms, Markov models, lazy learning algorithms, Bayesian statistics, a nonlinear observer, a sliding mode observer, an adaptive filter, a least means square adaptive filter, an augmented recursive least square filter, a dynamic Bayesian networks, combinations thereof, and the like. Other, non-limiting examples of optimization techniques include non-linear least squares, L2 norm, averaged one-dependence estimators (AODE), back propagation artificial neural networks, basis functions, support vector machines, k-nearest neighbors algorithms, case-based reasoning, decision trees, Gaussian process regression, information fuzzy networks, regression analysis, logistic regression, time series models such as autoregression models, moving average models, autoregressive integrated moving average models, classification and regression trees, multivariate adaptive regression splines, and the like.

Such a learning algorithm 305 may be used in real-time to improve the predictive power of the model 301 in conjunction with outcome feedback 304. In aspects, such a learning algorithm 305 may also be used to update the model 301 in conjunction with a training dataset 312. In aspects, the training dataset 312 may be provided as part of an updating algorithm (i.e. retraining of a local model 301 based on newly received population data, optionally combined with local herd historical data), as an initial training program, to refresh a corrupted dataset, etc.

Figure 5:
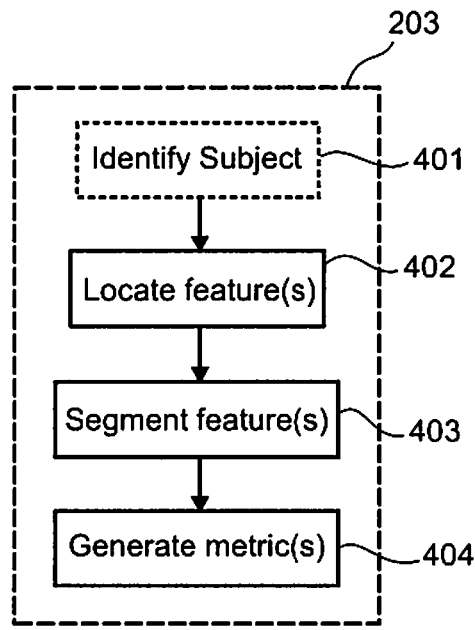
FIG. 5 shows aspects of a method for analyzing a feature in accordance with the present disclosure.

FIG. 5 shows aspects of a method for analyzing 203 a feature in accordance with the present disclosure. The method may include identifying a subject 401 (e.g. either by visual confirmation, RFID tag identification, a feature recognition algorithm, etc.). Such identification may be advantageous to ensure reliable recall of historical data for later steps in a process, for correlating changes in the subject with previous values, for recalling previous feature segmentations, previously confirmed feature shapes, previously confirmed feature location vectors, and the like.

The method may include locating a feature 402. A feature may be located by use of an expected-shape dataset (e.g. from previous measurements, a default database of shapes, etc.), from a previously determined location vector (from a vector relating one or more feature locations on a subject to one or more related features), though a preliminary thermal assessment (i.e. a whole body assessment to locate warm and cool regions of interest), combinations thereof, or the like. One or more images in a dataset may be scanned for the desired feature based upon such conditions, and the feature may be located and/or marked for further analysis.

The method may include segmenting a feature 403. The feature may be segmented so as to isolate an accurate region for further analysis. In aspects, the method may include a step of segmenting an udder, or portion thereof (e.g. a quarter udder, a teat, etc.) from one or more images of a cow (i.e. a subject in accordance with the present disclosure). Segmenting may be completed via a perimeter mapping algorithm, a shape matching algorithm, a color matching algorithm, a thermographic method, combinations thereof, or the like.

Steps of identifying a subject, locating a feature, segmenting a feature, and generating metric(s) from a feature maybe completed within a single image, or over a series of images captured during an analysis process.

In aspects, the steps of feature location and segmentation may be performed in the presence of an obstruction (i.e. an aspect of the subject or environment that blocks direct access to the entire feature of interest for the analysis). In such situations, an additional algorithm may be used to overlay the obstruction in combination with historical segmentation data, expected feature shapes, etc. in order to extract the desired features from images with only partial views thereof. In aspects, limited amounts of a feature may be segmented for analysis (e.g. a front portion of an udder, a portion of a face, etc.). Such algorithms may be employed to combine segmented portions of the feature of interest over a plurality of images, to generate a plurality of metrics based upon partial analyses, to generate a representative metric from collocated data across the plurality of images, etc. Such a configuration may be advantageous for improving a metric extraction process from a feature that moves, or may be at least partially obstructed across a plurality of pictures thereof.

The method may include generating one or more metrics from the segmented feature(s). Generation of metrics may include calculating an average parameter (e.g. color, temperature, volume, etc.), a gradient (e.g. a thermal gradient, a colorimetric gradient, etc.), a variance of a parameter (e.g. a color variance, a temperature variation, a maximum and minimum temperature, a standard deviation for a parameter, etc.), a thermal map (e.g. a topological map, a feature correlated map, etc.), from the feature for use in one or more analysis, predictions, etc.

The method may include steps of de-noising data, calibrating data against a reference, etc. before, during, and/or after a metric extraction process.

Figure 6:
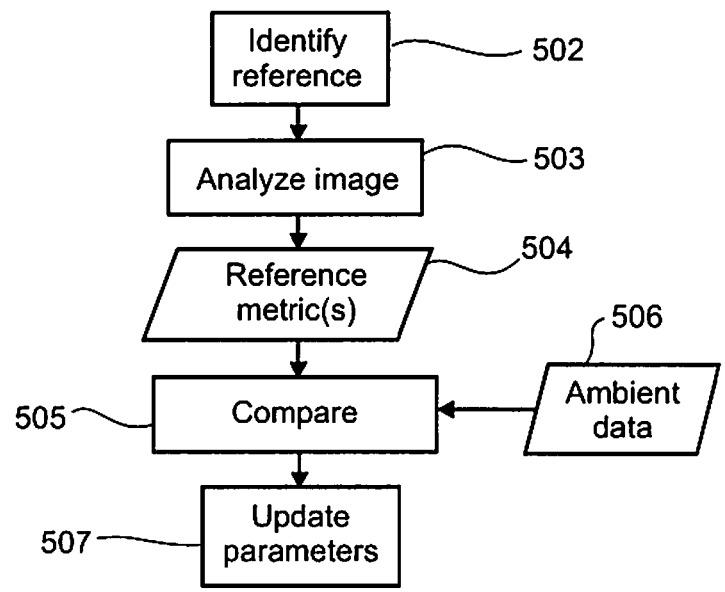
FIG. 6 shows aspects of a method for calibrating a system in accordance with the present disclosure.

FIG. 6 shows aspects of a method for calibrating a system in accordance with the present disclosure. The method may include identifying a reference 502 in one or more images captured by a camera in accordance with the present disclosure. Some non-limiting examples of references include a machine head, a fence post, a ventilation port, a wall, a reference pad (i.e. a pad with known colorimetric and/or infrared reflectance properties), or the like. The method may include analyzing the image(s) 503 to extract the reference from the image(s). Analyzing the image(s) 503 may be performed with methods similar to locating and/or segmenting a feature 401, 402 in accordance with the present disclosure. One or more metrics, such as average temperature, temperature gradient, or the like may be extracted from the reference and stored as a reference metric 504.

The method may include comparing 505 the reference metric 504 with one or more ambient data points 506 (e.g. a thermistor measurement, a weather report, an ambient temperature reading, etc.). The comparison 505 may be used to update calibration parameters 507 for the system. In aspects, the calibration procedure may be performed before and/or after a cleaning procedure, between cleaning of an associated environment (e.g. a facility, a pen, a milking station, before and after engagement of an infrared heating system, etc.), so as to ensure reliable operation of the system between changes in the local environment, over time, with the introduction of alternative lighting, heating sources, etc. In aspects, the calibration procedure may be used to generate a reliable operating configuration in one or more environmental configurations (e.g. summer, winter, hot, cold, dark, light, etc.). Such a configuration may be advantageous for minimizing false alarms associated with environmental changes that can occur during a monitoring process.

FIG. 7 shows a system for generating training data 609 in accordance with the present disclosure. The system may include a historical database 601, including such information as histories 606 relating to metrics, outcomes, external data, and the like relating to individual subjects 602, groups of subjects 603 (e.g. herds, crowds, families), similar breeds 604 (e.g. animals, and population subsets with similar physiological attributes, weights, lifespans, breeding characteristics, etc.), and entire subject populations (e.g. all the animals in a monitored population, within a geometric location, etc.), as well as external signals, ambient conditions 605, combinations thereof, and the like. The historical database 601 may be tapped to generate datasets of confirmed outcomes 608 for use in the generation of training dataset(s) 609. In aspects, the training data set 609 may be generated specific to a known subject (i.e. relying heavily on the extraction of historical data relating to the history 607 of an individual 602 subject), but training datasets may be generated from predominantly herd data 603, as well as other forms of data to suit the training process at hand.

Such training data 609 may be used to train and/or update a predictive model in accordance with the present disclosure directed at individual subjects, at herds, at families, at groups, or the like, so as to generate a more reliable predictive capability, to update models, etc.

In aspects, a system in accordance with the present disclosure may be configured to employ a plurality of predictive models (e.g. models directed at individuals, groups, herds, breeds, etc.) in order to improve the predictive capability thereof.

FIGS. 8a-b show a time history graph of metrics for evaluating the outcome of a subject in accordance with the present disclosure. FIG. 8a shows a graph of metric data (i.e. in this case, temperature data, and activity data) for purposes of illustration. The graph illustrates trends that may be extracted from a point history of measurements (e.g. daily, N times per day, measurement of metrics, etc.). In aspects, the moving average of a group of subjects 701 (e.g. a herd, a crowd, etc.) is shown with statistical variances 703a,b (i.e. plus or minus one standard deviation). The statistical variances of the herd may be generated from a statistical model, or as part of a predictive model each in accordance with the present disclosure.

A temporal trend of a metric (e.g. an average temperature of a feature, shape changes of a feature, mucus build-up, etc.) is shown for an individual subject 702, a member of the group of subjects. A can be seen in FIG. 8a, the metric for the individual subject 702 generally varies with the progression of time, more so than that of the group. Included in the graph are influencing parameters (i.e. parameters that have influence on the individual or group metrics, the modeling thereof, etc.). In aspects, the graph may include a trend for the ambient temperature 708 as well as for the average activity level of the herd 709.

At a present point in time 705, the individual subject is expressing a metric that is significantly higher than that of the group. A predictive model in accordance with the present disclosure may accept historical data trends from the individual 702, the herd 701, the ambient temperature 708, the average activity levels 709, among other inputs and generate one or more predictions as to the state of risk of the individual 702. As can be seen, a confidence interval 706a,b for future metrics for the individual subject 702 are shown in the figure. A range of criteria may be used to determine when a subject is considered at risk of a significant reduction in health.

FIG. 8b shows a risk metric trend 715 for the individual subject data of FIG. 8a. The risk metric trend 715 may be a deviation from a herd population norm (i.e. deviation from the herd mean temperature), an accumulating deviation therefrom, or the like. Such a risk metric may be advantageous for more easily making decisions based on obtained data, amid considerable herd and/or individual fluctuations.

The risk metric may include one or more criteria for assessing the severity of the risk level of an individual. Herein are shown a moderate risk level 711 and a severe risk level 712. As can be seen, at the time marker 705, the individual subject has entered into a state of moderate risk for the monitored outcome (i.e. in this case an outcome of mastitis). The individual passes from moderate risk to severe risk at the second time marker 725. In aspects, the predictive model may be used to generate an estimate of future risk from the present readings and historical trends, thus potentially indicating a severe risk level before it has actually occurred.

FIG. 9 shows a user interface for displaying data about a group of subjects in accordance with the present disclosure. Each individual in a group is labeled along a row (e.g. subject 1, subject 2, subject i, etc.) and a present and/or predicted/accumulated risk value for that individual is shown in adjacent columns. As can be seen, in this non-limiting example, the subject i 810 may be at high risk of having mastitis, with an even higher risk being apparent when considering the accumulated risk values and/or predictive outcome for the individual. In this case, subject i 810 is highlighted as part of an alert, which may be associated with a predictive method in accordance with the present disclosure.

In aspects, the system may be configured to employ methods for managing a self-cleaning camera module in accordance with the present disclosure. A self-cleaning method may include steps of evaluating the cleanliness of the window, determining if cleaning is necessary, if so cleaning the window in accordance with the present disclosure, if not continuing with operations (e.g. observing a target, operating the camera, collecting one or more image and/or video, etc.). The method may include continuing with operations for a predetermined length of time before re-evaluating the cleanliness of the window/lens, monitoring for an event that may preclude the cleaning process, etc. The step of evaluating may include analyzing an image taken by a camera in accordance with the present disclosure and comparing with one or more aspects of a reference image (post cleaned image, reference clean image, averaged values from a range of images, a reference target in an image, etc.). One or more aspects of the evaluating process may include assessing a differential map of the absorption through a window along the optical path (e.g. to search for one or more sites of fouling on the window, etc.). The method may include a step of test cleaning (e.g. a burst of dry air, etc.). The method may include comparing an image before and after a cleaning or test cleaning process in order to determine if the cleaning process has been successful or not. The method may include repeating the cleaning process if a previous cleaning step was ineffective.

In aspects, the system may be configured to employ a method for managing a self-cleaning camera module in accordance with the present disclosure including the steps of evaluating the cleanliness of the window, determining if cleaning is necessary, if so cleaning the window in accordance with the present disclosure, if not, closing a shutter (e.g. a protective cover in accordance with the present disclosure) and placing the camera module into standby. The method also includes watching for a subject (e.g. via a second camera system, a second camera module, a surveillance camera, etc.), waking and opening the shutter of the camera module (e.g. upon sighting of the subject, upon proper placement of the subject in the field of view of the camera module, etc.), continuing with operations (e.g. observing a subject, operating the camera, collecting one or more images and/or video, etc.).

In aspects, the step of watching for a subject may be performed by one or more sensing means (e.g. an RFID locating system, a pyrometer, an ultrasonic sensor, a light curtain, etc.). The sensing means may trigger a signal for the camera to wake-up and continue operations when a suitable subject is detected in range. In aspects, the subject may be an animal (e.g. a cow, a sheep, a lamb, a pig, etc.) equipped with an RFID tag. A RFID tag reader may be positioned near to the camera modules such that as a target moves within range of the reader, the camera may awaken and continue with operations (e.g. assessing cleanliness, obtaining a reading, etc.).

The method may include continuing with operations for a predetermined length of time before re-evaluating the cleanliness of the window/lens, monitoring for an event that may preclude the cleaning process, etc. The step of evaluating may include analyzing an image taken by a camera in accordance with the present disclosure and comparing with one or more aspects of a reference image (post cleaned image, reference clean image, averaged values from a range of images, a reference target in an image, etc.). One or more aspects of the evaluating process may include assessing a differential map of the absorption through a window along the optical path (e.g. to search for one or more sites of fouling on the window, etc.). The method may include a step of test cleaning (e.g. a burst of dry air, etc.). The method may include comparing an image before and after a cleaning or test cleaning process in order to determine if the cleaning process has been successful or not. The method may include repeating the cleaning process if a previous cleaning step was ineffective.

The method may include one or more of steps assessing energy reserves, assessing fluid reserves, scheduling maintenance, combinations thereof, and the like.

The method may also include analyzing the images received from the cameras to determine if a cleaning operation should be suspended until a more appropriate time. Such cleaning aspects may be suspended when system detects a suitable subject (e.g. an animal, a gas leak, an active manufacturing line, etc.) in the field of view of one or more of the camera module. Such suspension of cleaning may be performed until adequate analysis of the target can be completed and the associated camera module is free from more pressing matters (e.g. analyzing suitable targets, scanning for targets, etc.).

In aspects, the method may include assessing if the subject is within range and, if so, suppressing cleaning operations until the subject has left the field of view of the camera module, or a secondary camera module.

In aspects, the camera module may be included as part of a livestock management system (e.g. managing a milking process, reproductive scheduling, herd health monitoring, etc.). In such systems, the management of livestock movement is generally focused around feeding, shearing, and milking processes as well as monitoring of livestock during the mating season. The movement of animals within the farmyard may be broken down into aspects of free livestock traffic and controlled livestock traffic. The farms that make use of free livestock traffic are generally configured without gates and the livestock may decide how they want to move throughout the given space. In farms with controlled livestock traffic, the livestock remain in control of how they want to move, but their path may be restricted by means of gate systems and assets. In many systems with guided livestock traffic, the livestock often feed first before milking. Under this system, livestock are milked after having had access to food.

Such path planning may be considered when positioning a camera module in accordance with the present disclosure within the monitoring environment. In some livestock monitoring applications, such freedom of movement may necessitate attachment of the camera module in close proximity to the feeding station, milking station, and/or gates leading there to or there from. Thus the environment surrounding the camera module may be particularly prone to contamination.

In aspects, a system in accordance with the present disclosure may be used in combination with one or more systems for monitoring the feeding habits, eating levels, fluid analyte testing systems (e.g. milk, blood, fecal, urine analysis), as well as comparison with related metrics pertaining to the eating habits, milk production, milk quality, and the like of a subject, a group of subjects, etc.

The system may be coupled to one or more body feature related biometrics, including changes in the size/shape of one or more features, the cleanliness of one or more features, etc.

In aspects, the system may be configured to assess the fertility of an animal individually or amongst a herd. The fertility of the animal may be considered the outcome for the purposes of this discussion. In aspects, the system may be directed to analyze features of the muzzle and/or genitalia of the subject, in order to assess one or more metrics (e.g. thermographic data, color, size, engorgement, etc.). In aspects, the mucus around the muzzle of a subject may become thicker as well as hotter during times of ovulation. Monitoring such metrics over time may allow for mapping a fertility cycle, which may provide breeders with improved predictive capacity for creating ideal breeding conditions.

In aspects, a system in accordance with the present disclosure may compare data from a range of metrics. Including thermograms, collages, size, color, and shape variance of features, and the like, the system may obtain one or more metrics from related systems (e.g. a livestock management system, a milking machine, a diagnostic tool, a lab datacenter, etc.). Such information may include milk yield trends (such as decreasing milk yield may indicate the onset of sickness), cell count levels in blood, urine, and/or milk (increasing values usually indicate the onset of sickness), levels of salt in the milk, and conductivity levels of the milk (increases in conductivity may indicate the onset of sickness). A predictive model in accordance with the present disclosure may be configured to accept such data as it is available, for training purposes, for making predictions of outcome, etc. Such a configuration may be advantageous for providing a more robust confirmation of sickness, fertility, or the like.

In aspects, one or more segmented feature portions obtained from a plurality of images or a video sequence may be combined into a representative segmented feature for further analysis. In aspects, such an operation may be performed by locating common features between the plurality of segmented feature portions and stitching them together to form the representative segmented feature. In aspects, the plurality of segmented feature portions may be directly overlaid (i.e. in the form of a collage) onto each other in an analysis image in order to generate a representative image for further analysis. In such a non-limiting example, pixels related with the segmented feature that overlap during the overlaying process, may be averaged, etc. in order to generate a stabilized representative segmented feature.

In aspects, a system in accordance with the present disclosure may be configured to track one or more of cleanliness, gait, mucus formation, and the like as secondary measures of the health, and environmental aspects related to the health of the subject. Such a configuration may be advantageous for providing a more robust confirmation of sickness, fertility, frailty, or the like.

In aspects, a system in accordance with the present disclosure may be configured to capture one or more anthropomorphic aspects of the subject (e.g. udder characteristics, coat patterns [for identification], udder location with respect to one or more feature landmarks, facial characteristics, etc.). Such information may be used for purposes of identification, for tracking of changes in body features, for use in a segmentation process, etc.

Such a system may be advantageous for providing measurements of a subject without substantially interrupting workflow thereof (e.g. may be configured to analyze moving animals, capture data in compromised measurement situations, etc.)

In aspects, the step of segmenting a feature may be used to derive a size and shape statistic of an individual subject (e.g. an animal, a cow, etc.). Such information may be used in the metric extraction process, or may itself be a metric associated with the outcome of the individual.

In aspects, the metric may be provided in the form of a measurement vector (temperature statistics of the observed udder), a topological map, etc. which may be included along with information relating to the updated udder shape/size statistics of the individual subject.

The method of analyzing the metrics and formulating a prediction of risk, may make a comparison between the herd metrics (which may be considered normal for the purposes of analysis). The analysis may accept the measurement vector as well as temperature statistics, historical data, ambient data, combinations thereof, and the like.

In aspects, the prediction may highlight regions of the feature that are considered at risk, abnormal, etc. (i.e. highlight the quarter udder, teat, etc. that is at risk, unusually high temperature, etc.). Such information may be conveyed via an alert in accordance with the present disclosure.

In aspects, the features of interest may be located and segmented in a robust and predictable manner, in order to extract relevant measurement (temperature) values therefrom.

In aspects, the segmentation algorithm may include segmentation of a feature (e.g. an udder), segmentation of sub-features (e.g. a quarter udder, a teat, etc.).

In aspects, the method of locating a feature may include computing feature shape candidates, selecting a best fit feature shape based upon a comparison of the candidates to the image, the expected feature shape, or the localization of a sub feature (e.g. localization of one or more teats). The method of segmenting may include extracting one or more sub-features from a segmented feature, geometrically dividing sub-features from within a segmented feature or candidate feature shape, etc.

In aspects, the detection of the feature may be based upon the thermographic characteristics thereof. In one non-limiting example, an udder of a cow is one of the warmest features on the surface of the animal. A feature location algorithm for an udder, in accordance with the present disclosure may, at least in part, rely on the udder being a warm area in the image. Thus a location vector for the feature may be based upon determining the warmest area of an image.

In one non-limiting example, a box filter of a size half of the expected feature size may be used to extract candidate features from the image. Local maxima in the filter output may be considered feature position candidates.

In aspects, regions of images may be discarded from analysis as being too high or too low in temperature to be considered physiologically relevant to the indended analysis. In aspects, one or more regions of images may be considered as stationary (i.e., not containing any substantial motion over a sequence of frames). In aspects, such information may be discarded from analysis, used to determine environmental information, used to determine the location of a subject, or the like (i.e. often the subject will be substantially moving from frame to frame during an assessment thereof).

In aspects, at each feature position candidate, possible feature shapes may be computed and a segmented shape may be selected by comparing shape candidates with a database of expected shapes (e.g. default expected shapes, historical shapes, shapes from previous analyses, etc.).

In aspects, the method of segmenting a feature may include segmenting a feature from a feature position candidate, by applying a thermal thresholding and/or labeling algorithm to determine one or more udder shape candidates for each detected candidate position.

Candidate feature shapes may be further smoothed using one or more binary morphological operations, refining one or more feature shapes using GrabCut, combinations thereof, or the like.

In aspects, the method of segmenting may include selecting a segmented feature from the set of computed feature shapes using criteria based on image properties, expected feature shape, and sub-feature detection and localization, combinations thereof, and the like.

In aspects, the feature candidates may be selected by comparing the image properties to a set of udder shape candidates, including computing the area of each feature shape candidate (e.g. count the number of pixels, calculate an area, etc.), sorting the feature shape candidates by area, pixel count, etc., estimating the differential of the number of pixels with respect to the index of each particular feature shape candidate. In aspects, the differential may be regarded as the instability of the feature shape candidate, and the maximally stable feature shape candidates (i.e., the ones corresponding to local minima of the differential of the number of pixels) may be selected and placed into the candidate set, while the others may be discarded. From the remaining set of feature shape candidates, the system may select one of the more maximally stable candidates for further analysis and metric extraction.

In aspects, one or more feature shapes may be selected by parameterizing the feature shape (i.e. describing permutations of the feature via a limited number of shape parameters), and performing a model fit or likelihood score to each udder candidate determined by a previously computed expected udder shape (i.e. determining the optimal parameters satisfying the feature shape model from the image(s) under consideration). From the set of feature shape candidates, select the one or ones with best model fit.

In aspects, a method for segmenting a feature may include selecting one or more feature candidates based upon the detection of one or more sub features (e.g. teats, nostrils, fur patterns, etc.). In aspects, the method may include detecting possible sub features in the image, for example by using a trained detector from one or more example image(s). In one non-limiting example, such a process is implemented with a boosted cascade of detectors using Haar-filters. The method may include selecting feature candidates whose sub features best match those detected in the image(s).

In aspects, a method for extracting one or more metrics from a segmented feature may include measuring the maximum temperature, the average temperature, and/or the temperature variance is extracted in each selected feature and/or sub feature.

In aspects, the step of updating may include updating the expected feature shapes using at least a portion of the data determined in the previous analysis. In one non-limiting example, the "expected shape" may be updated and stored in the system using the measured feature shape obtained during the feature segmentation step, and/or generating a new "expected shape" from a combination of the most recently measured shape and the previous "expected shape(s)".

In aspects, the prediction may include accepting the metric measurement vector computed by the feature analysis step and comparing the vector to one or more previously collected statistics, thus creating an anomaly score.

In aspects, the statistics of an individual may be compared with those of the group in order to compensate for trends like time of day, air temperature, and the like.

In aspects, the system may generate a group set of statistics, in form of a parameter vector x describing the probability distribution of the feature metric statistics of the entire group of subjects as a single entity. In one non-limiting example, the statistics may be represented as a state vector (describing the mean of the probability distribution, the current expected value of the metric parameters, etc.), and a covariance matrix. Other representations (e.g. particle clouds) are envisaged.

The relationship between the expected statistics of an individual subject and the group may be described by an observation model for each individual subject. A prediction of the group statistics may be generated from the statistics stored at a previous time predicted to the current time using a prediction model in accordance with the present disclosure. The group statistics may be estimated from the measurements of one or more individuals within the group and the prediction of the group statistics generated by the prediction model. The statistics for a particular individual in the group may then be predicted based upon the updated group statistics.

An anomaly may be detected by comparing the predicted statistics for an individual subject and the measurements made upon that subject at any given time. If the deviation between the predicted and measured results greater than a predetermined threshold, the measurement is regarded as an anomaly.

In one, non-limiting example, the statistics may be represented with a state vector z and a covariance matrix C. The anomaly value may be computed as $a=(z_i-\tilde{z}_i)^T[(C+C_i)]^{\wedge}(-1)(z_i-\tilde{z}_i)$, where $C$ and $C_i$ are covariance matrices describing uncertainties in the group set statistics and the measurement respectively and $z_i$ is a measured state vector, while $\tilde{z}_i$ is a predicted state vector. If the value is greater than a predetermined threshold (i.e. such as may be determined by user-defined system sensitivity), the measurement is regarded as an anomaly. In aspects, a more robust detection may include an accumulation of the anomaly score over time (i.e. equivalently a risk score).

In aspects, the system may be configured to exclude low temperature anomalies from consideration (i.e. in the case of a mastitis detection system). In aspects, absolute thresholds may be set, so as to override a relative threshold setting. Such thresholds may be configured to be including or excluding. For example a lower threshold might be set telling that the deviation must be greater than an absolute number (of, e.g., degrees Celsius) in order to be counted as an anomaly. In aspects, one or more thermal parameters with deviations below a threshold may be excluded from the anomaly computation. In aspects, a high threshold might be set, such that temperature deviations above this threshold may always be counted as an anomaly.

In aspects, the updating process may include updating the data in the statistical and/or predictive model of the system, so as to maintain a strong predictive value therefrom during use. Such an updating process may include an adaptive or self-learning algorithm in accordance with the present disclosure. In one non-limiting example, the group statistics may be updated from the predicted group statistics and the measured individual member statistics with an Extended Kalman Filter in Joseph form.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. A system for predicting health outcome of a subject moving through an environment, the system comprising:
a camera situated within the environment and configured to generate one or more images or a video sequence including at least a portion of interest of the subject; and
a processor configured to identify and segment at least the portion of interest from the one or more images or the video sequence to form one or more segmented features, to calculate one or more metrics from the one or more segmented features, to calculate risk values based upon the one or more metrics for an interval of time, and to accumulate the calculated risk values with previously calculated risk values over a period of time, wherein the period of time includes multiple intervals of time, and to predict the health outcome of the subject based upon the accumulated calculated risk values,
wherein, when a first part of the portion of interest of the subject is obstructed and a second part of the portion of interest of the subject different from the first part is segmented to form partially segmented features, the processor is further configured to merge the partially segmented features to form the one or more metrics.

2. The system as claimed in claim 1, further comprising a database configured in communication with the processor and configured to store the one or more images or the video sequence, one or more reference features, the one or more segmented features, or the one or more metrics,
wherein the processor is configured to communicate with the database.

3. The system as claimed in claim 2, wherein the processor is configured to compare the one or more reference features with the one or more segmented features to predict the health outcome of the subject.

4. The system as claimed in claim 1, wherein the processor is configured to receive one or more environmental parameters, to calculate the one or more environmental parameters from the one or more images or the video sequence, or to use the one or more environmental parameters to assist in predicting the health outcome of the subject.

5. The system as claimed in claim 1, wherein the processor is configured to segment at least a portion of the feature from each of the one or more images or the video sequence to form a collection of segmented feature portions and configured to combine the one or more segmented feature portions to form a representative segmented feature for predicting the health outcome of the subject.

6. The system as claimed in claim 5, wherein the representative segmented feature represents substantially more of the feature than any one of the segmented feature portions.

7. The system as claimed in claim 1, wherein the processor is configured to identify an obstruction in the one or more images or the video sequence, the obstruction obscuring a part of the portion of interest.

8. The system as claimed in claim 7, wherein the obstruction is selected from the group consisting of a body part, a leg, a tail, a dirty lens, an object, a milking machine component, and a combination thereof.

9. The system as claimed in claim 1, wherein the camera is configured to generate the one or more images or the video sequence while the subject is moving within the environment.

10. The system as claimed in claim 1, wherein the camera is selected from the group consisting of a digital camera, a visible light camera, a near-infrared reflectance imaging camera, an infrared camera, a fluorescence imaging camera, a UV imaging camera, a thermal imaging camera, a 3D camera, and a combination thereof.

11. The system as claimed in claim 1, further comprising a plurality of cameras, each camera configured to image at least a portion of the feature, or an alternative feature on the subject.

12. The system as claimed in claim 1, wherein the processor is configured to send out an alert based upon the health outcome prediction.

13. The system as claimed in claim 1, wherein the subject is an animal or a lactating animal.

14. The system as claimed in claim 1, wherein the feature is selected from the group consisting of an udder, a part of an udder, a teat, a muzzle, a nostril, a hair pattern, a patch of skin, a hoof, a mouth, an eye, genitalia, and a combination thereof.

15. The system as claimed in claim 1, wherein the one or more metrics include thermographic data, color, shape, size data, a thermal metric, an average temperature, a thermal gradient, a temperature difference, a temperature range, a thermal map, a physiological parameter, changes therein, and a combination thereof relating to the one or more segmented features.

16. A method for predicting health outcome of a subject moving through an environment, the method comprising:
   imaging a portion of interest of the subject to produce one or more images thereof;
   identifying one or more features in the one or more images;
   segmenting out at least a portion of the identified features from the one or more images to form one or more segmented features;
   when a first part of the portion of interest of the subject is obstructed in the one or more images and a second part of the portion of interest of the subject different from the first part is segmented to form partially segmented features, merging the partially segmented features to form a representative segmented feature;
   calculating one or more metrics from the representative segmented feature;
   calculating risk values based upon the one or more metrics for an interval of time;
   accumulating the calculated risk values with previously calculated risk values over a period of time, wherein the period of time includes multiple intervals of time; and
   predicting the health outcome of the subject based upon the accumulated calculated risk values.

17. The method as claimed in claim 16, wherein the imaging is performed over a period of time while the subject is moving within the environment.

18. The method as claimed in claim 16, further comprising:
   segmenting out the one or more segmented features from the one or more images; and
   generating a representative segmented feature for calculating the one or more metrics.

19. The method as claimed in claim 16, wherein the imaging is performed before, during, or after a procedure, and
   wherein the procedure is selected from the group consisting of a milking procedure, administration of a medication, a mating process, a sporting event, and a training procedure.

20. The method as claimed in claim 16, further comprising comparing the one or more segmented features to a reference feature or to an environmental parameter from the subject as part of the prediction.

21. The method as claimed in claim 16, further comprising comparing the one or more segmented features or the one or more metrics to a previously obtained segmented feature or metric as part of the prediction.

22. The method as claimed in claim 16, further comprising comparing the one or more segmented features or the one or more metrics from the subject to those obtained from a family of related subjects, as part of the prediction.

23. The method as claimed in claim 16, further comprising alerting a user or system to the prediction.

24. The method as claimed in claim 16, wherein the health outcome is an infection.

25. The method as claimed in claim 24, further comprising identifying a location of the infection from the one or more images of the subject.

26. The method as claimed in claim 16, wherein the imaging is performed by at least one selected from the group consisting of a digital camera, a visible light camera, a near-infrared reflectance imaging camera, an infrared camera, a fluorescence imaging camera, a UV imaging camera, a thermal imaging camera, a 3D camera, and a combination thereof.

27. The method as claimed in claim 16, wherein the prediction is at least partially performed by a predictive model.

28. The method as claimed in claim 16, wherein the subject is an animal and the one or more features are selected from the group consisting of an udder, a part of an udder, a teat, a muzzle, a nostril, a hair pattern, a patch of skin, a hoof, a mouth, an eye, genitalia, and a combination thereof.

29. The method as claimed in claim 16, wherein the one or more metrics include thermographic, color, shape, size data, a thermal metric, an average temperature, a thermal gradient, a temperature difference, a temperature range, a thermal map, a physiological parameter, changes therein, or combination thereof relating to the one or more segmented features.

30. The method as claimed in claim 16, further comprising storing the one or more metrics or the representative segmented feature for future recall.

31. The method as claimed in claim 16, wherein the imaging is performed before, during, or after a procedure, and
   wherein the procedure is selected from the group consisting of a milking procedure, administration of a medication, a mating process, a sporting event, and a training procedure.

* * * * *